United States Patent [19]

Kalthoff et al.

[11] Patent Number: 4,579,004

[45] Date of Patent: Apr. 1, 1986

[54] INSTRUMENT FOR DETECTING THE INSTANT AT WHICH A CRACK BEGINS IN A MECHANICAL STRENGTH TEST OF A FERROMAGNETIC METAL

[75] Inventors: Jörg F. Kalthoff, Bad Krozingen; Siegfried Winkler, Freiburg, both of Fed. Rep. of Germany

[73] Assignee: Fraunhofer-Gesellschaft zur Förderung der angewandten Forschung e.V., Munich, Fed. Rep. of Germany

[21] Appl. No.: 652,320

[22] Filed: Sep. 19, 1984

[30] Foreign Application Priority Data

Sep. 24, 1983 [DE] Fed. Rep. of Germany ....... 3334570

[51] Int. Cl.⁴ .................. G01N 3/30; G01N 19/08
[52] U.S. Cl. ............................................ 73/799; 73/12
[58] Field of Search .......................... 73/799, 12, 844

[56] References Cited

U.S. PATENT DOCUMENTS 3,482,437 12/1969 Martens ................................. 73/799
4,418,563 12/1983 Kalthoff et al. ....................... 73/799

Primary Examiner—Anthony V. Ciarlante
Attorney, Agent, or Firm—Frishauf, Holtz, Goodman & Woodward

[57] ABSTRACT

The moment of beginning of fracture in breaking strength tests of ferromagnetic samples (7) is detected by the spreading of a magnetic field out of the incipient crack in the magnetized sample by means of a magnetic probe (23). Until the beginning of the crack, the magnetic field runs through the magnetized sample. The voltage induced in the magnetic probe at the moment the crack starts is used to stop a time measuring counter which was reset and turned on at the beginning of the stressing of the sample.

11 Claims, 5 Drawing Figures

INSTRUMENT FOR DETECTING THE INSTANT AT WHICH A CRACK BEGINS IN A MECHANICAL STRENGTH TEST OF A FERROMAGNETIC METAL

This invention concerns an instrument for use in a fracture toughness measurement of samples of iron, steel, or other ferromagnetic metals by detecting the instant at which a crack beings following the application of stress to the sample, and thereby tripping a time measurement counter which was started when the stress was applied. A known instrument for such purposes is described in published German Application DE-OS No. 30 44 841. With that device it is possible to determine the impact fracture toughness of materials on the basis of previously established impact reaction curves when an impact test measures time at which fracture sets in. for determining the impact reaction curve the shadow technique caustic method is used with reference to a suitable comparison material in order to obtain the strain intensity factor as a function of time. The known device is based on the recognition that the time course of the strain intensity factor depends only upon the leastic behavior of the sample & hammer system and holds for steels of different toughness so long as the elastic properties of the steels themselves are the same and the conditions are fulfilled that there by no plastic zones around the tip of the crack.

In the case of the known device the fracture occurrence time is determined by means of an electronic counter which is started by a first signal and stopped with a second signal. The first signal is obtained by means of a strain gauge strip disposed on the hammer edge of an impact device, with the rising edge of the hammer signal being interpreted as the beginning of the impact event. The signal for stopping the counter that occurs at the beginning of cracking is detected by means of a second strain gauge strip which is laterally disposed on the sample next to the point of a notch which has been put in the sample.

Since the samples must be provided with a strain gauge strip in advance of the actual impact test in order to determine the time the fracture begins, in addition to the costs of the strain gauge strip there is also the time requirement for adhesively applying the strain gauges.

SUMMARY OF THE INVENTION

It is an object of the present invention to provide an instrument of the kind above described in which the stop signal for the time measuring unit is generated simply and without contact with the sample.

Briefly, use is made of the ferromagnetic properties of the sample and means are provided for magnetizing the sample as well as means for detecting a magnetic field change. The origination of a crack, which is to say the beginning of the propagation of a crack in the beginngin of a fracture, produces a gap in the sample that causes magnetic field lines to spread outward out of the surface of the sample. These lines of force are detected by means of a magnetic probe in order to generate a stop signal for the time measurement device at the onset of fracture.

The magnetization apparatus can be a d-c generator by means of which a pulse of current is made to pass through the sample in order to obtani magnetization of the entire sample. Another possibility for magnetizing the sample is to put a magnet on the sample in contact therewith. In a convenient embodiment of the invention the magnet can be a horseshoe-shaped permanent magnet that is disposed on the side of the sample opposite to the side on which the magnetic probe is located or even on the same side on which the magnetic probe is located. At any rate, the magnet magnetizes at least the region of the expected crack. The magnetic probe can be constituted as a Hall probe, magnetic diode, air-core coil or iron-core coil. Preferably it is constituted in the manner of a sound recording or pick-up magnetic head of a magnetic tape recorder/reproducer.

BRIEF DESCRIPTION OF THE DRAWINGS

The invention is further described by way of illustrative example with reference to the annexed drawings, in which.

DESCRIPTION OF THE PREFERRED EMBODIMENT

Figure 1:
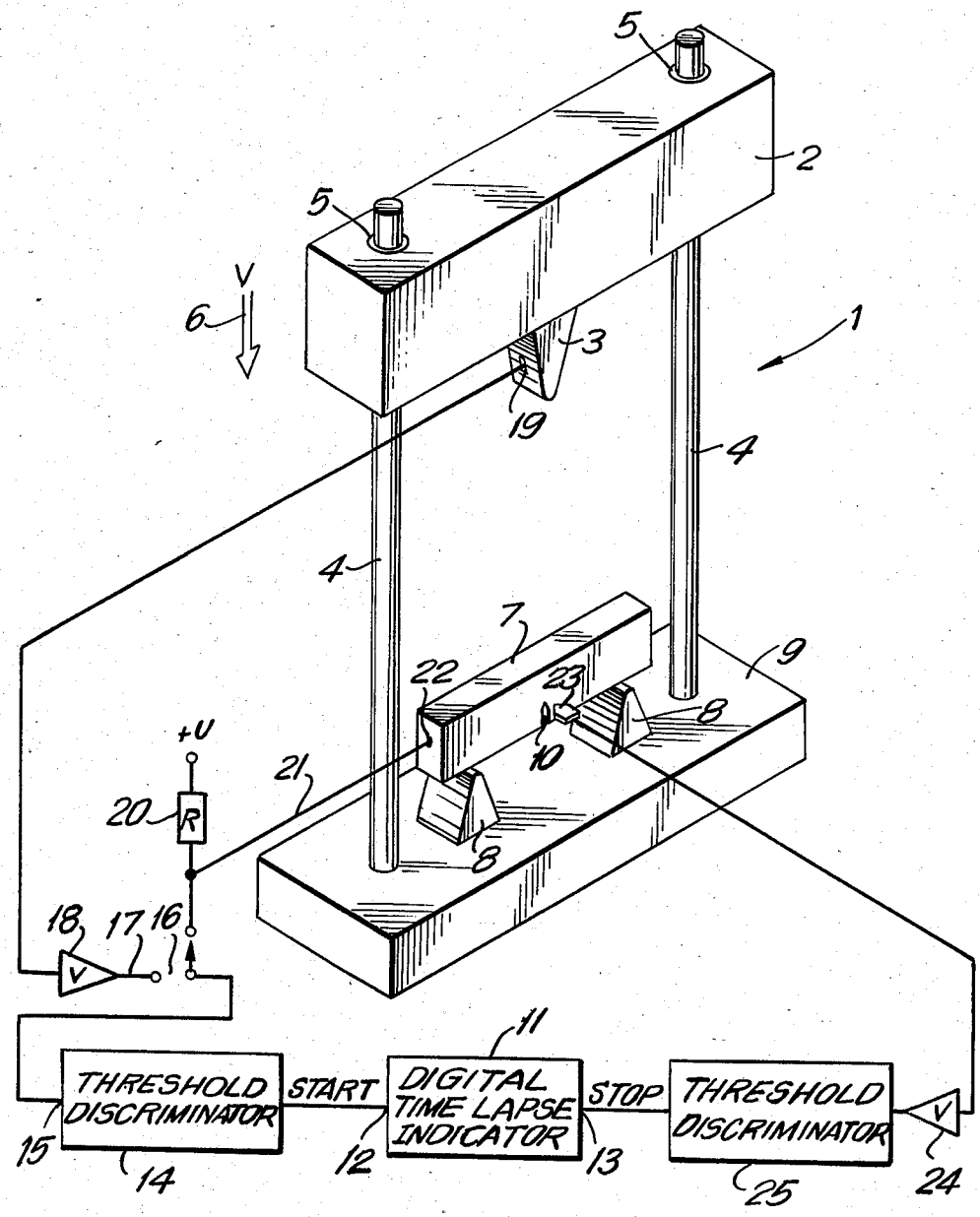
FIG. 1 is a prespective view of a weight-dropping apparatus equipped with an incipient crack detector according to the invention for determining the beginning of fracture, with timing and electronic equipment shown in block diagram.

FIG. 1 shows a weight drop apparatus 1 equipped according to the invention for magnetic detection of the beginning of fracture. The weight drop apparatus 1 comprises a drop hammer 2 with a hammer peen 3. The drop hammer 2 with its hammer peen 3 are guided in the vertical direction by means of two guide columns 4 which extend upward through busings 5 in the drop hammer 2. After the massive drop hammer 2 is raised up, it is first held and then released to fall by means not shown in the drawing. It moves then by its own weight with increasing velocity v in the direction of the arrow 6 until the hammer peen 3 hits the ferromagnetic metal sample 7 of which it is desired to determine the fracture toughness.

The sample 7 rests on two supports 8 which, like the guide columns 4, are supported on a table 9.

For determining the time duration between the encountering of the sample 7 by the hammer peen 3 and the beginning of fracture, at which latter event the start of a crack occurs at the point of a notch 10 in the sample, a time measuring device 11 schematically shown in FIG. 1 is provided.

The time measuring device 11 provides digital indication of the passage of time and has a start input 12 and a stop input 13. A signal at the start input 12 has the effect of resetting the time measurer and beginning the measurement. The time measurer can for example consist of a digital counter which is reset upon occurrence of a pulse at its start input and then counts the pulses of a clock pulse generator until a signal appears at the stop input 13. The count value, corresponding to the time that has elapsed between the occurrence of the start signal at the start input 12 and the stop signal at the stop input 13 is registered on the digital indicator of the time measurer. Of course it is also possible instead of direct digital indication to provide a print-out by means of a printer or to process the measured time periods with a computer.

The start input 12 is connected to the output of a first threshold value discriminator 14 which has an input 15 which can selectively be switched by the transfer switch 16 either to the sample 7 or to the output 17 of an amplifier 18. According to the position of the switch 16, the start signal for the determining of the time between the encounter of the hammer peen 3 with the sample 7 and the beginning of fracture at the point of the notch 10, i.e. fracture incidence time of the sample, either by means of a circuit that can be closed by the hammer peen 3 or else by means of an uncalibrated strain gauge strip 19 which is adhesively affixed to the hammer peen 3.

For the position of the switch 16 shown in FIG. 1, a voltage $+U$ is applied through an input resistor 20 to the input 15 of the threshold discriminator 14. The electric potential reaches the sample 7 through a conductor 21 and a contact 22. The contact 22 can be fixed directly on the sample 7 or on one of the supports 8. Upon incidence of the hammer peen 3, which is connected to the grounded pole of the voltage source through the drop hammer 2, the guide columns 4 and the table 9, a voltage drop is produced at the input resistor 20 which is detected by the threshold discriminator 14 and triggers the start of the time measurer 11.

When the switch 16 is not in the position shown in FIG. 1, the output of the amplifier 18 is connected with the input 15 of the threshold discriminator 14. The amplifier 18 amplifies the output signal of the strain gauge strip 19 which provides a measure for the force developed at the hammer peen 3. The rising edge of the hammer signal obtained by means of the strain gauge 19 is recognized by the threshold discriminator 14 at the beginning of the impact event and utilized for starting the time measurer 11.

After the start of the time measurer 11, the dynamic strain intensity factor rises in the course of the impact test in a manner corresponding to the individual impact reaction curve as a function of time. The curve of the dynamic strain intensity factor quantitatively reproduces the sample reaction to the impact event. It depends only on the elastic behavior of the sample hammer system and represents an unambiguous characteristic for this system. It holds particularly for all steel samples of the same size which are tested under the same conditions. The curve is the same, for example, for steels of different toughness, so long as these have the same elastic properties and the conditions are fulfilled that no plastic zones are near the tip of the crack.

Once an impact reaction curve is measured, it is then possible to determine the dynamic fracture toughness of a given steel by measuring only the fracture onset time in an impact test using the weight drop apparatus 1.

When a crack start or crack propagation appears at the tip of the notch 10 after the fracture on said time corresponding to the particular fracture toughness of the sample 7, this is determined by means of a magnetic probe, for example a magnetic audio head 23 which provides an output signal through an amplifier 24 and a second threshold discriminator 25 to the stop input 13 of the time measurer 11. In this manner the time measurer 11 determines the time lapse between the beginning of the impact event and the start of a crack, i.e. the fracture onset time.

Figure 2:
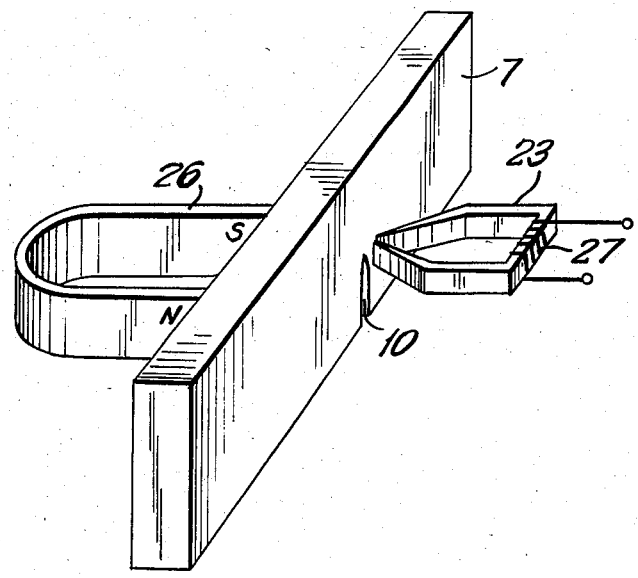
FIG. 2 is a perspective view on a larger scale, leaving out other components, of the sample under impact test, the magnetizing magnet and a magnetic head serving as the magnetic probe.

The magnetic audio head 23, the sample 7 and the permanent magnet 26 are schematically shown in perspective in FIG. 2. Whereas the sample 7 illustrated in FIG. 1 had already been magnetized by a current impulse, or by an external magnetic field applied for the period of time, the sample 7 in FIG. 2 is magnetized by means of the permanent magnet 26 in the region of the notch 10. The spacing of the magnetic head 23 disposed above the point of the notch 10 away from the sample 7 is about 1 mm. The gap width of the magnetic head can for example 3 $\mu$m, its impedance 35 ohms, and its inductance 120 mh.

When the fracture onset time is reached with the start of a crack, the magnetic field which up to that point was running through the material of the sample 7 spread out of the surface of the sample 7 as a result of the incipient fracture. In consequence a voltage is induced in the coil 27 of the audio magnetic head 23 which stops the time measurer 11, operating through the amplifier 24 and the threshold discriminator 25.

The permanent magnet 26 can, as shown in FIG. 2, be disposed either on the back side of the sample 7 or on the same side as the magnetic head 23. What is important is merely that the region of the point of the notch 10 is subjected to magnetic flux, so that when a fracture occurs in this region a magnetic field change will be produced in the surrounding air, which can be detected by the magnetic head 23, some kind of coil, a Hall generator or a magnetic diode.

The fracture time measured by means of the abovedescribed instrument makes it possible, by reference to a previously determined impact reaction curve, which needs to be carried out only once for a particular equipment, to measure the impact fracture process, making unnecessary any calibration of the instrumentation of the hammer and sample. For different impact devices a set of related impact reaction curves for determining the fracture toughness characteristics can be determined by the shadow optical caustic method for each stressing device and each sample geometry.

The crack start recognition by means of the audio magnetic head 23 or from other magnetic probe described with reference to FIGS. 1 and 2 can also find application in slowly developing fracture tests or experiments in which strainelongation diagrams are measured. In such fracture tests or experiments it is possible to recognize the moment of crack start precisely by means of the above-described apparatus.

Figure 3:
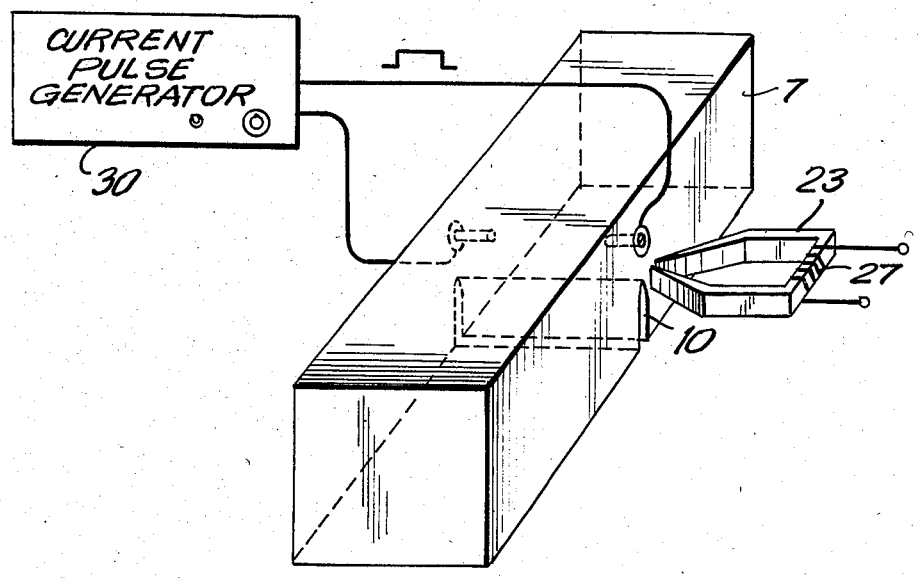
FIG. 3 is a schematic diagram illustrating magnetization of a test sample by passing a current impulse therethrough.

FIG. 3 illustrates the previously mentioned possibility of magnetizing the sample 7 by means of impulsive current, sometimes referred to as a current shock, through the sample. The current generator 30 magnetizes the sample 7 by putting a current impulse through the sample 7. It may then be disconnected before the hammer test. FIG. 3 shows the sample in position in the apparatus with the magnetic probe 23 as in FIG. 2, but the current impulse does not need to be put through the sample when it is already in the apparatus, provided that the procedure is standardized. Putting it through the sample when it is in position will of course produce a reaction in the probe 23, and this may be used to verify that the same magnetization impulse is used in all tests.

Figure 4:
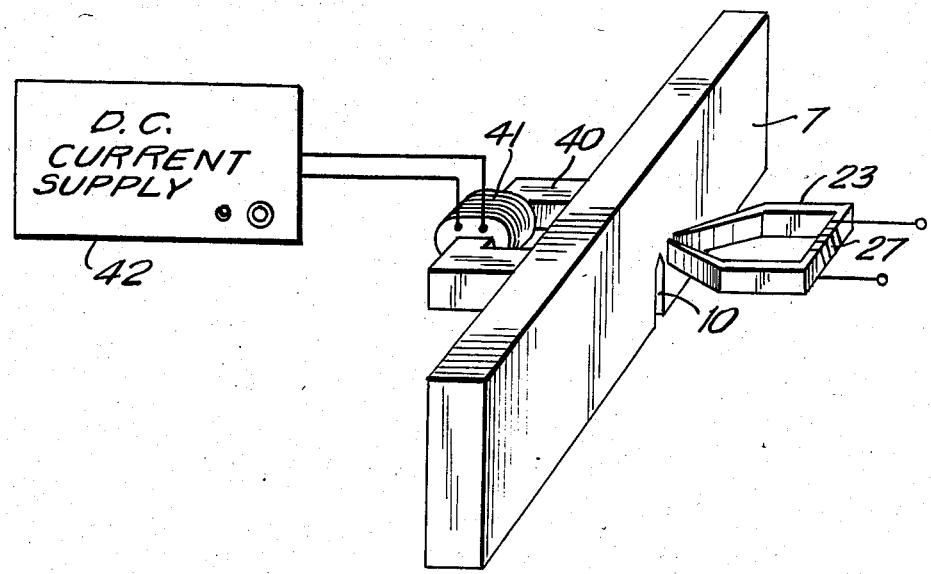
FIG. 4 is a schematic diagram illustrating magnetization of a test sample by means of an electromagnet.

FIG. 4 shows the use of an electromagnet 40 equipped with a winding 41 and supplied with a constant level of direct current by a d.c. current supply 42. In this case, the current is continuous at a constant level during the test. The electromagnet adheres by magnetic attraction to the sample 7. If desired, the magnet coil 41 could be simply slipped on over the sample 7, if made of a suitable size, but the arrangement of FIG. 4 is more convenient.

Figure 5:
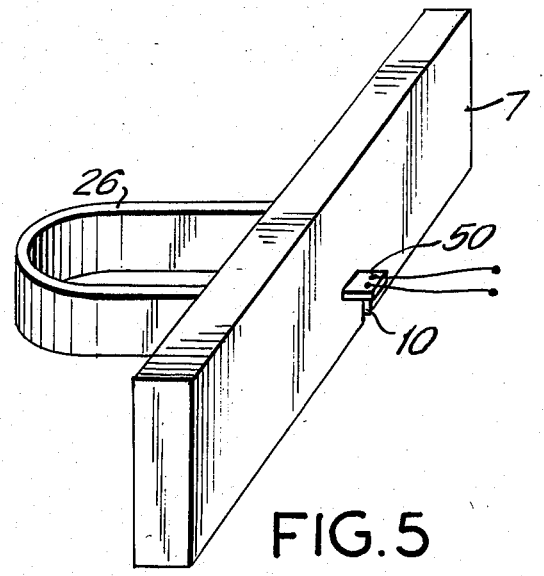
FIG. 5 is a schematic diagram illustrating the use of a Hall generator as a magnetic probe.

FIG. 5 illustrates the use of a Hall generator 50 as the magnetic probe, instead of the audio magnetic head 23 shown in FIGS. 2, 3 and 4. The Hall generator 50 is preferably a Hall IC, an electronic integrated circuit with a built-in preamplifier having a suitable threshold, so that the signal comes on strongly at its output as soon as a magnetic field change in excess of some predetermined small value takes place. Such Hall ICs are well known for the control of brushless d.c. motors, for example.

Although the invention has been described with reference to a particular illustrative example, it will be recognized that variations and modifications are possible within the inventive concept.

We claim:

1. Instrumentation for detecting the beginning of cracking in a mechanical fracture test of a ferromagnetic material sample, said sample having a notch (10) running across it for providing a preferred orientation for cracking under impact and being held and subjected to impact in an apparatus including an impact member disposed for producing cracks in said orientation at said notch, a start-stop time measuring device and means for starting said time measuring device in response to impingement of said impact member on said sample, comprising means (26) for magnetizing said sample in a manner producing magnetic lines of force in said sample running from one side of said notch to the other
   and a magnetic probe (23) adjacent to and spaced from said sample disposed and connected for stopping said time measuring device in response to a magnetic field change produced by the beginning of a crack in said sample.

2. Instrumentation according to claim 1, in which said means for magnetizing said sample are constituted by means for passing current through said sample at least for a short interval of time.

3. Instrumentation according to claim 1, in which said magnetization means is a magnet (26) in contact with said sample.

4. Instrumentation according to claim 3, in which said magnet is a permanent magnet.

5. Instrumentation according to claim 3, in which said magnet is an electromagnet.

6. Instrumentation according to claim 1, in which said magnetic probe is a Hall generator.

7. Instrumentation according to claim 1, in which said magnetic probe includes a detection coil (27).

8. Instrumentation according to claim 7, in which said coil is wound on a core, said coil and core being constituted in the configuration of an audio magnetic head of the type used for recording or reproducing sound on or from a magnetic tape.

9. Instrumentation according to claim 1, in which said time measuring device has a start signal input electrically connected with said sample for applying a potential to said start signal input that changes abruptly upon contact of said impact member with said sample.

10. Instrumentation according to claim 9, in which said sample is connected through a series resistance with an ungrounded pole of a voltage source and said impact member is connected with a grounded pole of said voltage source.

11. Apparatus according to claim 9, in which said impact member is equipped with a strain gauge strip for detecting the stress of impact of said impact member on said sample, and in which a threshold value detector is interposed at the input of said time measuring device and a selector switch is interposed at the input of said threshold value detector for selectively connecting the input of said threshold value detector to the output signal of said strain gauge of said impact member or to the potential of said sample.

* * * * *